United States Patent [19]

McMorris et al.

[11] 4,410,711
[45] Oct. 18, 1983

[54] METHOD FOR THE SYNTHESIS OF LEPIOCHLORIN, AN ANTIBIOTIC

[75] Inventors: Trevor C. McMorris, La Jolla; John R. Donaubauer, San Diego, both of Calif.

[73] Assignee: The Reagents of the University of California, Berkeley, Calif.

[21] Appl. No.: 278,100

[22] Filed: Jun. 29, 1981

[51] Int. Cl.³ .......................................... C07D 307/32
[52] U.S. Cl. .................................. 549/313; 549/323; 549/324
[58] Field of Search ...................... 260/343.6; 549/313

[56] References Cited

U.S. PATENT DOCUMENTS 2,726,250  12/1955  Clauson-Kaas .................. 260/343.6

FOREIGN PATENT DOCUMENTS 73,382  11/1951  Denmark .......................... 260/343.6
48-15932  5/1973  Japan .............................. 260/343.6

*Primary Examiner*—Ethel G. Love
*Attorney, Agent, or Firm*—Joseph E. Mueth

[57] ABSTRACT

A method for the synthesis of lepiochlorin, an antibiotic.

2 Claims, 2 Drawing Figures

LEGEND:

▨ NORMAL BACTERIAL GROWTH

▨ DECREASED GROWTH

☐ COMPLETELY INHIBITED GROWTH

● 6.5mm DIAMETER DISK

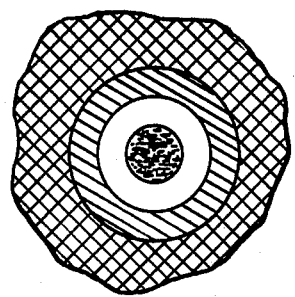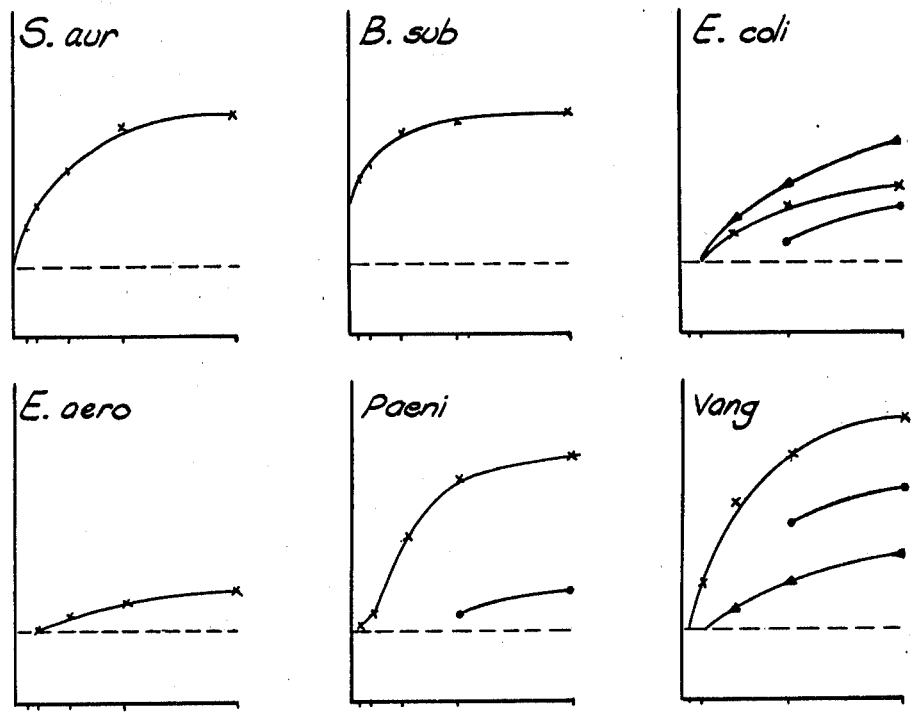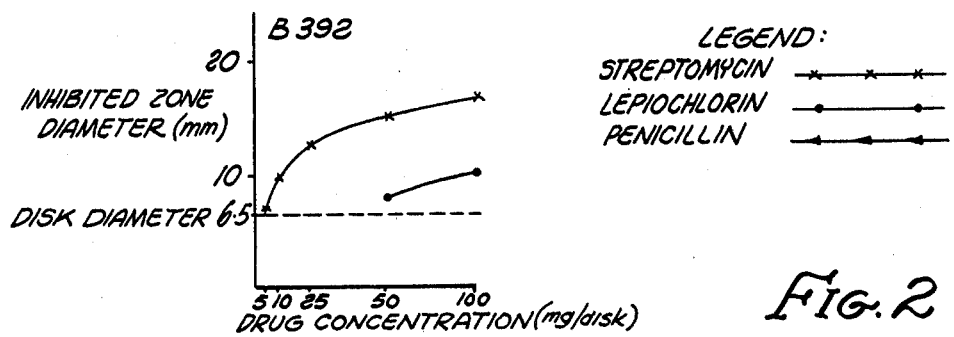
FIG. 1
FIG. 2

METHOD FOR THE SYNTHESIS OF LEPIOCHLORIN, AN ANTIBIOTIC

BACKGROUND OF THE INVENTION

The cultivation of certain fungi as a major source of food by some species of ants has been reported, A. Hervey, C. T. Rogerson, and I. Leong, *Brittonia*, 29, 226 (1977). It was reported recently that one such fungus, a Lepiota species, when grown in the laboratory produces a chlorinated antibiotic, lepiochlorin, for which the following structure was proposed by M. S. R. Nair and A. Hervey, *Phytochemistry*, 18, 326, (1979):

According to the present invention we have discovered a method for synthesizing this potentially valuable antibiotic. This novel method promises to be simpler and more efficient as a means for obtaining the drug, and it is to be expected that our method will supercede the method heretofore reported in the literature.

The invention described herein was made in the course of work under a grant from the Department of Health and Human Services.

SUMMARY OF THE INVENTION

Briefly, the present invention involves one or more of the following methods leading to the production of lepiochlorin.

$CH_2=CH-CH_2OH$ + (Reaction A)

allyl alcohol $CH_3-O-CH_2-CH_2-O-CH_2-Cl$ +

B-methoxyethoxymethyl chloride $\left(\begin{array}{c}CH_3\\|\\HC\\|\\CH_3\end{array}\right)_2 N-CH_2CH_3 \longrightarrow$ diisopropylethylamine $CH_2=CH-CH_2O-CH_2-O-CH_2CH_2-O-CH_3 \xrightarrow[\text{acid}]{\text{meta-chloro-peroxy-benzoic}}$ allylmethoxyethoxymethyl ether $CH_2-CH-CH_2-O-CH_2-O-CH_2-CH_2-O-CH_3$
$\phantom{CH_2-}\backslash_O\phantom{-}/$ glycidylmethoxyethoxymethyl ether (1)

$\underset{\underset{\text{ethyl 2-bromopropionate}}{}}{CH_3-\overset{Br}{\underset{|}{C}}H-\overset{O}{\underset{\|}{C}}-O-C_2H_5}$ + (Reaction B)

sodium thiophenoxide $\xrightarrow{THF}$ Ester $\xrightarrow{KOH/H_2O}$ 2-phenylthiopropionic acid $\xrightarrow{\text{lithium diiso-propylamide}}$ dianion of 2-phenylthiopropionic acid (2)

(Reaction C)

1 + 2 $\longrightarrow$ mixed isomeric lactones (3)

(Reaction D)

3 + meta-chloroperoxybenzoic acid $\longrightarrow$ sulfoxide $\xrightarrow[\text{Benzene}]{\text{Reflux}}$ unsaturated lactone (4)

(Reaction E)

4 $\xrightarrow{\text{HCl}}{\text{THF}}$ alcohol (5)

(Reaction F)

5 + thionyl chloride + pyridine $\longrightarrow$ chloride (6)

(Reaction G)

6 + N-bromosuccinimide $\xrightarrow{\text{benzoyl peroxide}}$ bromo-chloro-lactone (7)

-continued (Reaction H)

7 + silver acetate + acetic acid ⟶ 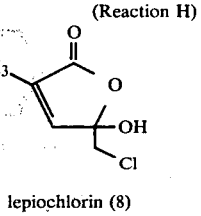

lepiochlorin (8)

Alternatively, reaction H can be carried out simply be refluxing the bromo-chloro-lactone in a solvent such as tetrahydrofuran, preferably in the presence of finely divided silica.

It is an object of this invention to provide a novel method of synthesis.

More particularly, it is an object of our invention to synthesize lepichlorin.

These and other objects and advantages of our invention will be apparent from the detailed description which follows.

DESCRIPTION OF THE PREFERRED EMBODIMENTS

The following examples are presented solely to illustrate the invention and are not limiting in any way. In the examples, the parts and percentages are by weight unless otherwise indicated. The reaction conditions are clearly variable in the context of this invention since those skilled in the art will readily recognize that parameters such as reaction times, solvents, temperatures and product recovery techniques are not fixed and may be varied considerably with the aid of the present general directions.

EXAMPLE 1

Preparation of Glycidylmethoxyethoxymethyl Ether 1.5 equivalents of β-methoxyethoxymethyl chloride in dichloromethane was treated with a solution of 1.5 equivalents of a 7.7 molar solution of diisopropylethylamine in dichloromethane over a period of 5 minutes. 1.0 equivalent of neat allyl alcohol was then added over a period of 3 minutes. After stirring for 10 minutes the reaction mixture had warmed to reflux. The reaction mixture continued to reflux for approximately 15 minutes and was then left to cool to ambient temperature overnight. The reaction mixture was concentrated in vacuo to ⅓ of the original volume and extracted with 2.5% HCl. This solution was then dried with $MgSO_4$. After removal of the drying agent and solvent the residue was distilled at reduced pressure. The yield of allylmethoxyethoxymethyl ether (boiling point 42° C. at 2–3 mm. of Hg.) as a clear, colorless mobil liquid was 79%.

1.0 equivalent of allylmethoxyethoxymethyl ether was dissolved in dry dichloromethane and treated with 1.1 equivalents of meta-Chloroperoxybenzoic acid. This mixture was then refluxed overnight and the solvent was removed in vacuo. The residue was filtered through alumina and then distilled at reduced pressure. The yield of glycidylmethoxyethoxymethyl ether (boiling point 53°–55° C. at 0.25 mm of Hg.) was 79%.

EXAMPLE 2

Preparation of 2-Phenylthiopropionic Acid

More particularly, 1.0 equivalent of a 0.6 molar solution of ethyl-2-bromopropionate in THF was added to a suspension of 1.5 equivalents of sodium thiophenoxide in THF. This mixture was then stirred overnight. The reaction mixture was diluted with water, made basic and extracted with dichloromethane. The organic extracts were combined, dried and freed from solvent. This ester was hydrolyzed by suspending the oil in water and heating in the presence of potassium hydroxide. The mixture was acidified and extracted with ethyl ether. The ethyl ether extracts were combined, dried, freed of solvent and distilled. The yield of 2-phenylthiopropionic acid was 81%.

EXAMPLE 3

Preparation of Lactones (3)

1.0 equivalent of a 1.0 molar solution of 2-phenylthiopropionic acid in THF was added to 2.2 equivalents of a 1.0 molar solution of lithium diisopropylamide in THF under $N_2$ at −60° C., over a period of 15 minutes. The reaction mixture was left to stir at −60° C. for approximately 1 hour, warmed to −20° C., stirred for 45 minutes and cooled to −60° C.

1.4 equivalents of a 1.4 molar solution of glycidylmethoxyethoxymethyl ether in THF was added over a 10 minute period. The reaction mixture was maintained at −60° to −70° C. for 3 hours and then left to warm to ambient temperature overnight. The reaction mixture was then diluted with aqueous ammonium chloride and ethyl ether. The layers were separated and the pH of the aqueous layer was adjusted to pH 5.0 and then extracted with ethyl ether. The organic extracts were combined and dried. After removal of the drying agent and solvent the residue was dissolved in benzene and a small amount of silica gel was added. This mixture was then heated in a Dean-Stark apparatus for 1 hour to complete the lactonization. This mixture was extracted with saturated sodium carbonate, water, and saturated sodium chloride solution and dried. The mixture of lactones that remained was chromatographed to give lactones (3) in a yield of 98%.

EXAMPLE 4

Preparation of Unsaturated Lactone (4)

1.0 equivalent of a 44.0 mMolar solution of lactones (3) in dichloromethane were cooled to −15 C. and treated with 1.0 equivalent of meta-chloroperoxybenzoic acid for 45 minutes. The reaction mixture was poured into aqueous sodium carbonate. The layers were separated and the organic was dried. After removal of drying agent and solvent the residue was dissolved in benzene and heated to reflux to 1 hour. Purification by silica gel chromatography gave the desired unsaturated lactone (4) in 90% yield.

EXAMPLE 5

Preparation of the Alcohol (5)

To 1.0 equivalent of a 31 mMolar solution of unsaturated lactone (4) was added 10 equivalents of 3 molar HCl. This mixture was refluxed for 6 hours, neutralized, saturated with sodium chloride and extracted with ethyl acetate. After drying the residue was purified by chromatography on silica gel which gave an 85% yield of the alcohol (5). NMR δ1.90(t, 3H, J=1.5 Hz.) δ3.77(ABX m, 2H,); δ5.0(m, 1H); δ7.11(m, 1H).

EXAMPLE 6

Preparation of Chloride (6)

4.8 mmol of alcohol (5) was dissolved in 10 ml of spectral grade chloroform. 1.0 equivalent of pyridine and 1.05 equivalent of thionyl chloride were added under $N_2$ to the reaction mixture. This mixture was refluxed for 1.5 hour, cooled and the solvent was removed in vacuo. The residue along with $MgSO_4$ was added to a soxhlet thimble and extracted overnight with ethyl ether. After removal of the solvent the residue was Kugelrohr distilled to give the chloride (6) in a 74% yield. NMR $\delta 2.01$(t, 3H, J=1.6 Hz); $\delta 3.72$(ABX m, 2H); $\delta 5.18$(m, 1H); $\delta 7.22$(m, 1H). MS m/e 146.0148 (10), $C_6H_7O_2Cl$; 97.0289 (100), $C_5H_5O_2$.

EXAMPLE 7

Preparation of Bromo-Chloro-Lactone (7)

Allylic bromination of 6 was effected by refluxing the solution in carbon tetrachloride for about 26 hours in the presence of N-bromosuccinimide (1.5 equiv) and a little benzoyl peroxide. Bromination occurred almost exclusively in the desired position. The bromo-chloro-lactone (7) was obtained as an oil: NMR $\delta 2.00$, d, J 1.5 Hz, 3H; 4.17 AB m, 2 H; 7.16 m, 1 H.

EXAMPLE 8

Preparation of Lepiochlorin (8)

Treatment of a solution of (7) in THF with an aqueous solution of silver acetate containing a trace of acetic acid afforded a crystalline lactone, mp 74°–74.5° C., 65% from 6, MS m/e 162.0109 (0.13) $C_6H_7O_3Cl$, 113.0237 (100) $C_5H_5O_3$, whose NMR spectrum was identical to that reported for lepiochlorin (8). Comparison with an authentic sample (mp 74°–74.5° C., mixed up undepressed, infrared spectrum) confirmed the identity.

Alternatively, The bromination mixture was cooled, freed of N-bromo succinimide and benzoic acid and concentrated in vacuo to a thick oil. This was dissolved in wet THF (about 5% $H_2O$), silica was added and the mixture refluxed for six hours. The silica was separated by filtration and the solution was dried with $MgSO_4$. Removal of solvent and drying agent left a whitish solid which was recrystalized from $CHCl_3$/Hexane. (Yield, 65%) of lepiochlorin (8).

Turning to the drawings:

FIG. 1 depicts certain zones, as explained hereinbelow, having reference to the testing of the antibiotic synthesized in accordance with this invention.

FIG. 2 depicts, in graph form, comparative test results, comparing lepiochlorin with several other known antibiotics.

TABLE I

| | BIOASSAY OF LEPIOCHLORIN: | | | | | | | |
|---|---|---|---|---|---|---|---|---|
| Conc. | S. aur | B. sub | E. coli | E. aero | Paeni | Calb. | Vang. | B-392 |
| 10 μg | 0/0* | 0/0 | 0/0 | 0/0 | 0/0 | 0/0 | 15/11 | 9/0 |
| 25 μg | 0/0 | 0/0 | 8/0 | 51/0 | 0/0 | 0/0 | 20/16 | 12/0 |
| 50 μg | 0/0 | 0/0 | 10/8 | 11/0 | 0/8 | 0/0 | 21/16 | 14/8 |
| 100 μg | 13/0 | 16/slght. | 14/11 | 14/0 | 0/10 | 51/0 | 24/19 | 16/20 |

S. aur = Staphylococcus aureus  
B. sub = Bacillus subtilis  
E. coli = Escherchia coli  
E. aero = Enterobacter aerogenes  
Paeni = Pseudomonas aeruginosa  
Calb = Candida albicans - yeast  
⎫ Human pathogens Vang = Vibrio anguillarum  
B-392 = Benechea harvey  
⎫ marine bacteria

*numbers given are zone diameters including disk of 6.5 mm diameter. First number is zone of decreased growth. Second number is complete inhibition zone. These zones are shown in FIG. 1 of the drawings.

Turning to FIG. 2 of the drawings, lepiochlorin is compared with the well-known antibiotics streptomycin and penicillin. These tests were made against a variety of bacteria. The inhibited zone disk diameter in millimeters is plotted along the vertical axis and the drug concentration in mg/disk along the horizontal axis.

Having fully described the invention, it is intended that it be limited only by the lawful scope of the appended claims.

We claim:

1. The method of preparing lepiochlorin which comprises reacting:

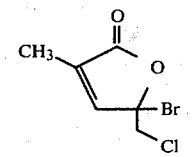

with silver acetate in the presence of a trace of acetic acid, and recovering lepiochlorin.

2. The method of preparing lepiochlorin which comprises reacting:

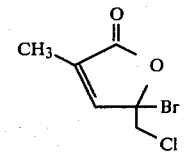

in tetrahydrofuran as a solvent, wherein finely divided silica is added prior to refluxing, and recovering lephiochlorin.

* * * * *